(12) United States Patent
Lowery

(10) Patent No.: US 7,066,955 B2
(45) Date of Patent: Jun. 27, 2006

(54) HIGH REFRACTIVE INDEX COMPOSITIONS USEFUL FOR INTRAOCULAR LENSES AND METHODS FOR MAKING SAME

(75) Inventor: Michael D. Lowery, Vista, CA (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 0 days.

(21) Appl. No.: 10/676,579

(22) Filed: Sep. 30, 2003

(65) Prior Publication Data

US 2005/0070626 A1   Mar. 31, 2005

(51) Int. Cl.
*A61F 2/14* (2006.01)
*C08G 77/20* (2006.01)

(52) U.S. Cl. .................. 623/6.11; 424/427; 428/405; 523/113; 524/588; 528/43; 623/6.56

(58) Field of Classification Search ............... 524/588; 424/427; 523/113; 528/32, 43
See application file for complete search history.

(56) References Cited

U.S. PATENT DOCUMENTS

| | | | | |
|---|---|---|---|---|
| 4,269,993 A | * | 5/1981 | Ohtake et al. | 556/450 |
| 4,418,165 A | * | 11/1983 | Polmanteer et al. | 523/210 |
| 4,560,711 A | * | 12/1985 | Suzuki | 523/212 |
| 5,008,305 A | * | 4/1991 | Kennan et al. | 523/212 |
| 6,630,560 B1 | * | 10/2003 | McGill et al. | 528/25 |

FOREIGN PATENT DOCUMENTS

EP    236674 A2  *  9/1987

OTHER PUBLICATIONS

Abstract of GB 611700.*

* cited by examiner

*Primary Examiner*—Marc S Zimmer
(74) *Attorney, Agent, or Firm*—Advanced Medical Optics, Inc.

(57) ABSTRACT

An intraocular lens suitable for implantation into an eye has an optically clear, deformable lens body composed of a silicone polymer and a silica reinforcer that structurally reinforces the polymer. The silica reinforcer is chemically modified with aryl groups effective to increase the refractive index of the silica reinforcer, preferably so as to substantially match the refractive index of the silicone polymer.

30 Claims, No Drawings

HIGH REFRACTIVE INDEX COMPOSITIONS USEFUL FOR INTRAOCULAR LENSES AND METHODS FOR MAKING SAME

FIELD OF THE INVENTION

The present invention relates to intraocular lenses, compositions useful for making such lenses and compounds, useful for making such compositions. The invention is particularly related to high refractive index intraocular lenses materials composed of silicone polymers and silica reinforcers useful in making such lenses and silicon-containing copolymers useful in making such compositions.

BACKGROUND OF THE INVENTION

Current intraocular lenses (IOLs) are often inserted into the eye through a small scleral tunnel incision. As is appreciated by those skilled in the art, successful implantation of the IOL requires it to have sufficient structural integrity and elasticity, and a sufficiently small size to permit deformation and insertion through the incision. Some representative IOLs and surgical procedures are described by Doyle et al U.S. Pat. No. 5,423,929 and Brady et al U.S. Pat. No. 5,476,513, the disclosure of each of which is incorporated herein in its entirety by reference.

Silicone polymers mechanically reinforced with a silica material have been developed as an optical material for IOLs. The small size requirement for the lens makes it advantageous that it also has a high refractive index. Accordingly, the silicone polymer of the IOL preferably is selected to have a high refractive index, generally of 1.42 and above. Inasmuch as such silicone polymers alone often lack adequate mechanical strength, a silica reinforcer, for example, fumed silica particles, is often finely distributed in the silicone polymer. Exemplary reinforced silicone elastomers for use in these IOLs have been described by Christ et al U.S. Pat. Nos. 5,376,694; 5,494,946; and 5,661,195, the disclosure of each of which is incorporated in its entirety herein by reference. A particularly preferred crosslinkable silicone copolymer of these previous IOLs is a polydimethyldiphenylsiloxane having the following formula:

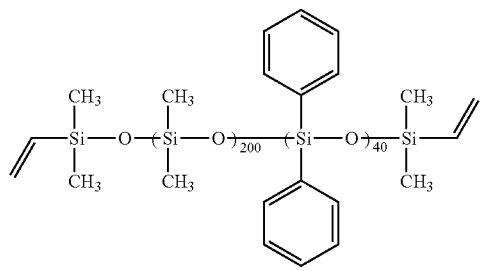

Previous IOLs, however, suffer from a tendency of the silicone copolymer to "crystallize" whenever the mol % of diphenyl in the molecule is increased in an effort to raise its refractive index. Such crystallization, which is believed to be due to the close packing and alignment of phenyl rings in the molecule, causes the optical properties of the IOLs to be compromised.

In an effort to prevent or reduce crystallization, Yang et al U.S. Pat. No. 5,512,609 have proposed raising the refractive index of the crosslinked silicone polymer to at least 1.50 by inserting a spacer group between the aryl group and the silicon atom, thereby permitting increased flexibility in the molecule. In this approach, a polymeric resin component preferably is employed to reinforce the lens body, with the polymeric resin component being selected so that its index of refraction is substantially matched to that of the silicone copolymer.

There continues to be a need to provide novel IOLs having high refractive indexes, preferably above about 1.46. Such IOLs should permit reduced thicknesses and smaller incisions while retaining good optical and mechanical properties.

SUMMARY OF THE INVENTION

New compounds, compositions which can be made from such compounds and intraocular lenses having lens bodies that comprise such compositions have been discovered. The present compositions comprise a silicone polymer, preferably a crosslinked silicone polymer, and a silica reinforcer including at least one aryl group, preferably a phenyl group, effective to increase the refractive index of the silica reinforcer relative to a similar silica reinforcer without at least one aryl group. The use of a silica reinforcer including at least one aryl group allows the silica reinforcer to be more compatible, in terms of refractive index, with silicone polymers which have refractive indexes greater than about 1.42, for example, at least about 1.46 or about 1.47 or about 1.5 or higher.

Conventionally, alkyl substituted silicon-containing compounds, such as hexamethyldisilazane, are used to cap the $S_i$—OH groups of a silica reinforcer used to reinforce a silicone polymer. This treatment, however, leaves the silica with a relatively low refractive index of about 1.46. In accordance with the present invention, a silica reinforcer including at least one aryl group has a higher refractive index, preferably a refractive index which substantially matches of the silicone polymer being reinforced, to afford an optically clear composition advantageously useful for producing intraocular lens bodies.

The present intraocular lenses are effective to be implanted in a mammalian, for example, human or animal, eye. Such lenses have a deformable lens body including a optically clear material comprising a silicone polymer, and a silica reinforcer present in an amount effective to reinforce the polymer. The silica reinforcers includes at least one aryl group effective to increase the refractive index of the silica reinforcer relative to a similar silica reinforcer without at least one aryl group. Advantageously, the present intraocular lens bodies include the reinforced compositions of the present invention, as described herein.

In one embodiment, the silica reinforcers of the present invention include covalently bonded silicon-containing moieties including at least one aryl group. Such moieties preferably include 1 to about 3 aryl groups per silicon atom. The aryl content can be varied depending on the desired refractive index of the final silica reinforcer.

The silicone polymer and the silica reinforcer preferably each have a refractive index of above about 1.46, for example, at least about 1.47 or about 1.5 or higher.

The silicone polymer preferably includes aryl groups, more preferably selected from substituted and unsubstituted phenyl groups, substituted and unsubstitued styryl groups and mixtures thereof. The silicone polymer advantageously is a crosslinked polymer, more preferably a crosslinked polysiloxane. Very useful silicone polymers include crosslinked silicone copolymers of (1) at least one polysiloxane including aryl groups, and (2) at least one crosslinker component.

Although any suitable polysiloxane including aryl groups may be employed, in one embodiment the polysiloxane has the formula:

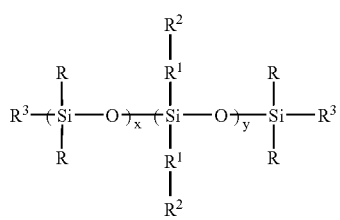

wherein each R is independently selected from the group consisting of alkyl radicals, substituted alkyl radicals cycloalkyl radicals, substituted cycloalkyl radicals, aryl radicals and substituted aryl radicals, each $R^1$ is independently selected from the group consisting of divalent hydrocarbon radicals and substituted divalent hydrocarbon radicals, each $R^2$ is independently selected from the group consisting of aryl radicals and substituted aryl radicals, each $R^3$ is independently selected from the group consisting of monovalent hydrocarbon radicals having a multiple bond and substituted hydrocarbon radicals having a multiple bond, x is an integer in a range of 0 to about 500, and y is an integer in a range of about 6 to about 500.

Preferably, each —$R^1$—$R^2$ is independently selected from a styryl radical and substituted styryl radicals. Advantageously, each —$R^1$—$R^2$ is the same. Because of the two spacer moieties —$R^1$— bonded to a single silyl group, the aryl content of the polysiloxane component can be increased, relative to polysiloxanes including no or only one spacer moiety, without unduly reducing the flexibility of the crosslinked silicone copolymer. For example, the aryl content of the polysiloxance can be greater than about 20%, such as in the range of about 16% or about 20% to about 25% or about 30% or more of the total silicon-bonded substituents on the polysiloxane. In terms of x and y in the above-noted formula, the ratio x/y preferably is less than about 4. Further, in the above-noted formula, each R preferably is methyl and/or each $R^2$ preferably is phenyl and/or each $R^3$ preferably is vinyl and/or each $R^1$ preferably is independently selected from methylene radical and ethylene radical.

Any and all features described herein and combinations of such features are included within the scope of the present invention provided that the features of any such combination are not mutually inconsistent.

These and other aspects of the present invention are apparent in the following detailed description of the invention.

DETAILED DESCRIPTION OF THE INVENTION

The present invention is directed to new compounds, compositions which can be made from such compounds and intraocular lenses (IOLs) having lens bodies including silicone polymers and silica reinforcers. Associated methods of IOL manufacture, methods of IOL use and methods of silica treating are also contemplated.

The present IOL lens bodies have chemical compositions that include silicone polymers, preferably crosslinked silicone copolymers. The proportion of the silicone polymer attributable to arylsilyl units may be selected to control or adjust the refractive index of the silicone polymer, and ultimately of the composition and the IOL lens body. Preferably such aryl silyl units, preferably more arylsiloxane units, are present in the silicone polymer in an amount to increase the refractive index of the polymer, more preferably in an amount of at least about 16 mol % or more of the total units making up the polymer.

Any suitable silicone polymer, preferably crosslinked silicone polymer, may be employed provided that it is suitable for use and functions effective as a material of construction for a deformable IOL lens body. A number of such silicone polymers are conventional and well known in the art.

In a very useful embodiment, the silicone polymer is obtained by crosslinking one or more compounds, which are actually uncrosslinked polymers or prepolymers, having the following structural formula:

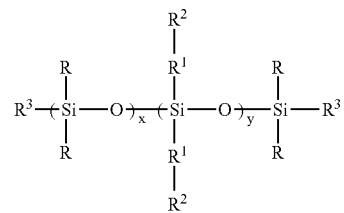

In the above formula, the Rs, $R^1$s, $R^2$s and $R^3$s are as described elsewhere herein.

The $R^1$ groups of the formula may be considered divalent spacer groups or radicals which, without limiting the invention, are believed to serve to separate the $R^2$ groups from the silicon atoms. Preferably, each $R^1$ is a substantially hydrocarbon, e.g., alkylene, arylene, alkarylene, or aralkylene and the like, divalent radical. Among such radicals are included, without limitation, methylene, ethylene, propylene, butylene and the like.

A convenient method of forming such linkages involves addition of Si—H across an unsaturated moiety of an organic compound, such as by a hydrosilation reaction coupling the organic compound to an appropriate H-silane or siloxane. Different geometric isomers are possible for larger groups than vinyl, therefore giving rise to different geometric isomers in the same arylsiloxane group whereby structurally different —R$^1$—R$^2$ groups would be present.

Each of the R$^2$ groups of the above formula is an aryl group, preferably having from 6 to about 10 carbon atoms. The aryl group can be unsubstituted or covalently bonded to one or more substituents, such as alkyl, alkenyl aryl, aralkyl, alkaryl, aralkenyl, alkenaryl, cycloalkyl, halogen, nitro, and the like. Preferably, each R$^2$ is selected from a phenyl group, a mono-lower alkyl-substituted phenyl group, a di-lower alkyl-substituted phenyl group and the like. Each R$^2$ can be the same as or different from the other R$^2$ of the arylsiloxane unit or the other R$^2$s of the compound.

In one very useful embodiment, each R$^1$ and R$^2$ in the formula together define a substituted or unsubstituted styryl group, in which case R$^1$ represents an ethylene diradical and R$^2$ represents a substituted or unsubstituted phenyl group. Advantageously, all the —R$^1$—R$^2$ groups in the compound are the same.

To further illustrate the arylsiloxane units of the above-noted compounds, the following exemplary structures are provided, which are by no means exhaustive:

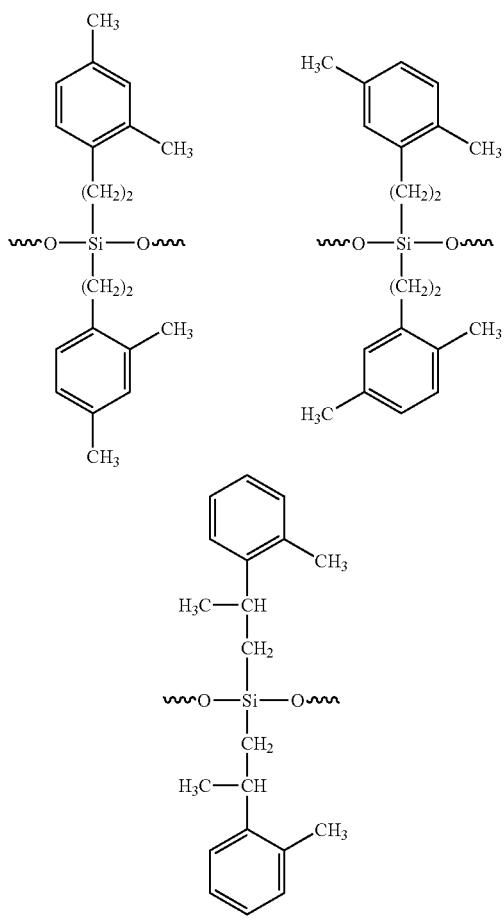

The compounds or oligomers of the present invention can be prepared by contacting a cyclic hydrosiloxane with an aryl compound capable of reacting with the cyclic hydrosiloxane under hydrosilation conditions. The reaction may be catalyzed, for example, using one or more platinum group metal components, many of which are commercially available and conventionally used in vinyl/hydride addition curing of silicone polymers. The amount of platinum group metal, preferably platinum, component employed is effective to promote the desired hydrosilation step. Such amount may be within the range of about 0.01 part per million (ppm) to about 100 ppm (or more) by weight of the total reactants present. The hydrosilation reaction is conducted at conditions effective to provide the desired product. For example, temperatures in the range of about 10° C. or lower to about 60° C. or higher may be employed. Contacting times in the range of about 10 minutes to about 10 hours or longer have been found to be useful. Since the desired hydrosilation reaction is often exothermic, the temperature of the reaction mixture may advantageously be controlled, e.g., by a cooling medium, to maintain the temperature in the desired range.

Alternately, the coupling of aryl group to silicon can be accomplished using a Grignard-type reaction. In such a reaction, the cyclic hydride-containing siloxane monomer is contacted with the appropriate aryl Grignard reagent at effective reaction conditions to produce the desired cyclic aryl-containing siloxane monomer. Such Grignard reaction conditions include, for example, reaction temperatures in the range of about −60° C. or lower to about 0° C. or higher, and reaction times are in the range of about 10 minutes to about 10 hours or longer.

The present compounds preferably are blocked at both ends with trisubstituted siloxane units. At least one substituent of the end-blocking group, represented by R$^3$, preferably contains an olefinic bond. The remainder of the substituents on the end-blocking group, represented by R, are not critical and each may be independently selected, for example, from among alkyl, aryl, substituted alkyl, substituted aryl groups and the like. Preferably, the R$^3$ substituent is an alkenyl group, such as a vinyl group, which permits curing or crosslinking of the compound to form a crosslinked silicone polymer.

The balance of the units of the compound or uncrosslinked polymer are typically dialkylsiloxane units, wherein each of the R groups bound to the silicon atom are independently selected. Preferably, the alkyl substituents are methyl groups. A compound or uncrosslinked polymer composed of the above-described units has a degree of polymerization (dp) of about 100 to about 2000.

Except to the extent that novel features are emphasized below, synthesis of a silicone copolymer having the above described structure can be performed in accordance with processes known in the art from starting materials that are either commercially available or made according to well-known state-of-the-art processes. Thus, in accordance with standard practice in the art, readily available cyclic oligomers of the components and precursors of the end-blocking groups are reacted in the presence of a suitable catalyst to achieve polymerization to the desired degree.

A reaction to provide the compound or uncrosslinked polymer is illustrated by reference to the following specific example. A mixture of cyclic octamethyltetrasiloxane, OH-terminated polydistyrylsiloxane, and 1,2-divinyltetramethyldisiloxane are reacted under base equilibration conditions in the presence of a polymerization catalyst, such as potassium silanolate, to afford the desired silicone polymer. The desired ratios of respective components in the polymer determine the ratios of reactants in the mixture.

In one particularyl useful embodiment, a degree of polymerization of about 250 is obtained. It should be specifically understood in connection with the preparation of the compound that after the composition of the compound is selected, the identification of suitable starting materials and ratios for polymerization is well within the skill of the ordinary artisan. Similaryl, the polymerization step can be conducted using a conventional catalyst, such as known N-catalysts and K-catalysts. For instance, the K-catalysts used can comprise potassium silanolate and potassium hydroxide, whereas the N-catalysts can comprise tetramethylammonium hydroxide. The degree of polymerization of the uncrosslinked silicone polymer is typically determined by observing the viscosity of the reaction mixture. The optical refractive index of the reaction mixture is also monitored and the reaction is not considered complete unless the reaction mixture has a viscosity within a desired range and an optical refractive index of at least about 1.44 or above about 1.46, for example, at least about 1.47 or about 1.50 or higher.

The desired viscosity range depends on the nature and composition of the polymer. For an uncrosslinked silicone polymer having dimethylvinylsiloxane end-blockers, about 20 mol % of distyrylsiloxane units with the balance being dimethylsiloxane units, and a dp of approximately 250, the desired viscosity range of the reaction product is about 2000 to about 2800 centipoise (cp). In this connection it is noted that whereas the aryl content of the polymer greatly influences the refractive index, the degree of polymerization does not. The degree of polymerization, on the other hand, greatly influences the viscosity of the polymer.

After the desired degree of polymerization and refractive index is achieved, the catalyst is inactivated, neutralized, or removed and the reaction product is carefully filtered, e.g., on a filter press, to remove any unreacted solid starting materials or other solid impurities. After filtration, volatile materials are carefully removed from the polymer by repeated exposure to vacuum, preferably while the copolymer is in a thin film form. The careful removal of volatiles, commonly termed "stripping", is considered important for the purpose of obtaining material suitable for use in an intraocular lens. The "stripping" is typically conducted in a state-of-the-art "wipe film evaporator" using large "wipe films" and the process is monitored by gas column chromatography of the removed volatiles. The removed volatiles are the residues of starting materials, cyclic and linear oligosiloxanes, and the like. Moreover, because in virtually every polymerization the molecular weight, or degree of polymerization, of the resulting polymeric products follows a substantially bell-shaped curve, the crude reaction product polymer also contains products having a substantially lesser degree of polymerization, than the desired dp. In this regard, it should be understood that a dp of 250 is to be construed as such dp numbers are normally construed in the art of polysiloxane chemistry. A dp of 250 thus means that the average dp of the polymeric product is about 250. Stripping of the copolymeric product is generally repeated several times, to remove a significant amount of the lower dp polymers, usually about 12 to about 16 percent by weight of the reaction product. It is considered important to monitor viscosity and refractive index at the end of the process of removing volatiles. As noted above, the desired viscosity depends on the precise nature of the "stripped" silicone copolymer, which is about 4100 to about 5300 cp.

The elastomeric IOL lens bodies of the present invention contain a silicone polymer, preferably a crosslinked silicone polymer, and a chemically treated silica reinforcer finely dispersed in the silicone polymer. It is preferred that the refractive index of the silica reinforcer is within about 0.015 of the corresponding refractive index of the silicone polymer, in order to prevent hazing in the lens body. The present treatment of the silica reinforcer is directed to increasing its refractive index above 1.46, for example to about 1.47 or higher or even to about 1.5 or higher.

Previous chemical treatments of silica reinforcers have employed trimethylsilyl chloride, as described in U.S. Pat. Nos. 3,341,490 and 3,036,985, the disclosure of each of which is incorporated in its entirety herein by reference. For instance, previously hexamethyldisilazane has been used to partially cap the Si—OH groups of fumed silica with trimethylsilyl groups. The resulting product, however, has a relatively low refractive index of about 1.46.

In order to generate a silica reinforcer having a higher refractive index, it is preferred that one or more silicon-containing compounds having at least one aryl group, i.e., silylating compounds used to modify silica, for example, fumed silica, be used. The refractive index thereby achieved can be above about 1.47, for example, about 1.47 or higher. Some exemplary compounds that can be used for this purpose are illustrated hereinbelow:

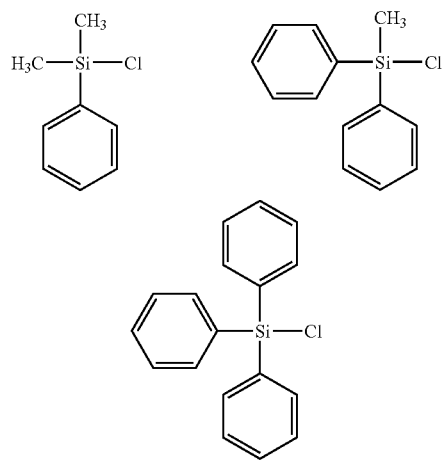

A silica reinforcer of the present invention is combined with the silicone polymer in an amount effective to reinforce the composition a ratio of preferably about 5 to about 45 parts by weight of the reinforcer in 100 parts of the final composition. In accordance with the present invention, the silica reinforcer preferably has a surface area of about 100 to about 450 $m^2/g$, more preferably at least about 200 $m^2/g$.

The chemical modification of the silica reinforcer, for example, of the surface of the silica reinforcer, can be performed in substantially the same step as when an uncrosslinked silicone polymer is intimately mixed with the silica. Intimate mixing is preferably aided by treating the mixture on a roll mill or like device. After intimate mixing, volatiles, such as unreacted silylating agent, gaseous by-products and water are removed from the mixture by heat and vacuum.

The intimate mixture of modified silica and uncrosslinked silicone copolymer may be considered the "base." For the purpose of making materials suitable for IOL lens bodies, the base is dispersed in a suitable inert solvent, such as trichlorotrifluoroethane (FREON) and the dispersion is filtered to remove any solid impurities. Thereafter, the solvent is removed by gentle heat and vacuum. The resulting, volatile-free, uncured (not yet cross-linked) base has a viscosity that permits intimate mixing of the base with a suitable catalyst and crosslinking agents, as well as subsequent manipulation for forming, preferably by molding, into IOL lens bodies. The viscosity range for this purpose preferably is about 35,000 to about 300,000 cp.

It is an important feature of the present invention that the uncured base have inherent characteristics of providing, after suitable curing by crosslinking, those physical properties highly advantageous for a soft intraocular lens. Thus, after the hereinafter described curing steps, the properties of the resulting crosslinked elastomer preferably are as follows:

an optical refractive index of at least about 1.44 or higher, such as at least about 1.46 or about 1.47 or about 1.50 or higher;
a Shore A durometer hardness value of at least 35;
a tensile strength of at least 500 psi;
a 150 percent minimum elongation (without damage), and
a tear strength of at least 20 pounds per lineal inch (pli).

The above-listed properties can be measured with state-of-the-art technology and instruments, for example, in accordance with the respective requirements of standard ASTM test methods. More particularyl, the durometer test is performed as ASTM D2240, the tensile and elongation tests as ASTM D412 and the tear strength test as ASTM D624 Die B.

Typically, the optical refractive index of the crosslinked elastomer obtainable from the base is at least about 1.46 or about 1.47 or higher or even about 1.5 or higher. In this regard, it is noted that crosslinking tends to slightly increase the optical refractive index as compared to the uncured base.

Preparation of the uncured base for crosslinking is accomplished as follows. The base is filtered once more, preferably through a 325 mesh screen to remove any remaining solid impurities. Thereafter, in accordance with standard practice in the art, the base is divided into two aliquots, preferably of equal weight. The aliquots are commonly termed "Part A" and "Part B", or first and second aliquot parts.

As is known in the art, crosslinking is accomplished by utilizing, for example, in a platinum catalyzed reaction, the terminal silicon bonded multiple bonds, preferably vinyl groups, of the uncrosslinked silicone polymer and the silicon-bonded hydrogen groups of the crosslinker component. The silicon bonded multiple bond groups are present both in the first and second aliquots of the base. Silicon-bonded hydrogen groups are added in the practice of the present invention to the second aliquot (Part B) in the form of one or more suitable crosslinking components. The crosslinking components per se are known in the art, and may be made in accordance with the teachings of U.S. Pat. No. 3,436,366, the disclosure of which is incorporated in its entirety herein by reference. Whereas a number of crosslinking components are suitable for practice of the invention, the liquid polyorganohydrosiloxane crosslinkers are eminently suitable and are commercially available. In order to have compatibility between the uncrosslinked silicone copolymer and the crosslinking component respecting the refractive index of refraction, it is preferred that the crosslinking component have a refractive index substantially the same, within about 0.05 and preferably within 0.02, as the polymer. Particularyl suitable are crosslinkers having the formula $R_2HSiO_{1/2}$, such as dimethylhydrosiloxane, monomethyl-, and phenyl-derivatives of this compound, and mixtures thereof.

The platinum catalyst can also be selected within the skill of the ordinary artisan, primarily from organoplatinum compounds, e.g., those of U.S. Pat. Nos. 2,823,218 and 3,159,601, the disclosure of each of which is incorporated in its entirety herein by reference. The platinum catalyst is added to the first aliquot (Part A).

In accordance with the invention, it is important that after mixing of the aliquots (Parts A and Parts B), the crosslinking should not proceed too rapidly at room temperature, thereby allowing at least about two, preferably about six hours, for work time with the mixed aliquots. For this reason, a small amount of suitable crosslinking inhibitor, such as 1,2,3,4-tetramethyl-1,2,3,4-tetravinyl cyclotetrasiloxane, is added to the second aliqout (Part B). Although the precise amounts can be adjusted within the skill of the ordinary artisan, the organoplatinum catalyst is often added to the first aliquot in an amount of about 4 to about 12 parts per million (ppm), preferably about 8 ppm, by weight. The crosslinking component is added to the second aliquot in the range of about 1 to about 6 parts per hundred by weight. The above specified inhibitor preferably is added to the second aliquot in an effective amount less than about 0.2 parts per hundred by weight. It has been found that best results are obtained when the amount of inhibitor used in the second aliquot is adjusted to provide about 6 hours of work time at room temperature.

In addition to the above-described crosslinking component and inhibitor, a UV absorbing material may optionally, and preferably, be mixed into the second aliquot, for example in accordance with the teachings of U.S. Pat. No. 4,868,251, the disclosure of which is incorporated in its entirety herein by reference. The ultraviolet absorbing material, which may be for example, a vinyl-functionalized 2-hydroxybenzophenone or a vinyl-functionalized benzotriazole, may be covalently linked to the copolymer of the composition during the crosslinking step.

A sample formulation summarized from those described above is given in the following table:

TABLE

| Material | Wt % in Intraocular Lens | |
|---|---|---|
| | Part A | Part B |
| Silicone copolymer | 79 | 76 |
| Modified silica reinforcer | 21 | 20 |

TABLE-continued

| Material | Wt % in Intraocular Lens | |
|---|---|---|
| | Part A | Part B |
| H-siloxane crosslinker | — | 3–4 |
| Platinum catalyst | 8 ppm | — |
| Crosslinker Inhibitor | — | <0.2 |
| UV Absorber | — | 0.1–1 |

Shaping of intraocular lens bodies from an elastomeric composition of the present invention may be accomplished by liquid injection molding or by cast or compression molding of the intimately mixed first and second aliquots. For instance, in the liquid injection molding process the mixed aliquots are injected into a hot mold kept at about 120° C. to about 150° C. The curing process is complete in about five minutes. In the cast or compression molding process, the mixed aliquots are placed into appropriate molds, and the molds are thereafter positioned in an oven heated to about 150° C. Under these conditions the cure is complete in about 15 to about 30 minutes. The cast molding process can also be completed at room temperature in significantly longer time periods.

Intraocular lenses made in accordance with the present invention have the above-described advantageous optical and mechanical properties.

The following non-limiting examples illustrate certain aspects of the present invention.

EXAMPLES

Example 1

Preparation of Crude Copolymer

In a 50 gallon reactor (Baker Perkins) mix octastyryl-cyclotetrasiloxane (86 kg), octamethyl-cyclotetrasiloxane (59 kg) and 1,2-divinyltetramethyl-disiloxane (0.6 kg) and heat under agitation and a nitrogen gas blanket to 100° C. When the temperature reaches 100° C. add 0.1 wt % N-catalyst (100 g). Continue heating and stirring and monitor the viscosity of samples taken from the reaction mixture. If after 45 minutes there is no change in viscosity, add 0.1 wt % more N-Catalyst (100 g). After a viscosity change has been observed and the styrylcyclics have dissolved continue heating and stirring for 3 hours. Then neutralize or destroy the catalyst, for example, by bubbling carbon dioxide into the mixture, or heating to 150° C. Viscosity of the cooled reaction mixture is between about 2000 to about 2800 cp, the refractive index is between about 1.49 and about 1.51.

Example 2

Purification of Copolymer

Filter the cooled reaction mixture on a filter press with a pressure of about 40 psi on five or more filter plates using Zeta Plus filter paper, catalog #A1311-10A. Strip the filtered copolymer at least three times on a "wipe film evaporator". Monitor the process of stripping by gas chromatography, taking samples of 1 g of the volatiles and dissolving the same in 3 g of hexane. Continue stripping until adequate devolatilization. Viscosity of stripped copolymer is between about 4100 to about 5300 cp, the refractive index is between about 1.49 and about 1.51.

Example 3

Formulation of Base Including Silica Reinforcer

In a 50 gallon mixer mix the stripped polymer (75 kg) with hexaphenyldisilazane (2 kg). Add MS-7 silica (20 kg, surface area 200 m2/g) in increments, and with last silica load add distilled water (20 kg), mix well. Thereafter, mill mixture twice on three roll mill, and return mixture to 50 gallon mixer. Heat mixer to reach internal temperature of 150–200° C. After 30 minutes of heating and stirring at above temperature, apply vacuum and continue heating for 2.5 hours while the mixer reactor is under vacuum. After cooling under vacuum, add more stripped polymer as a "cut-back" and mix well. Let a small sample of base settle (unstirred) for about 30 minutes and check viscosity at 25° C. with Brookfield viscometer. The viscosity is between about 35,000 to about 200,000 cp.

Example 4

Purification of Base

Disperse the base in trichlorotrifluoroethane (FREON) in a ratio of about 2 gallons of base to 1 gallon of FREON, and add about 0.5 gallon of diatomaceous earth to the dispersion for each 2 gallons of base. Filter the dispersion on a filter press using Zeta Plus filter paper, catalog #A1311-10A. Pressure during filtration should be kept at about 30 psi and should not exceed that value. Clear filrate is required. Place the collected clear filtrate in a reactor, and agitate under nitrogen purge. Apply vacuum gradually while purging slowly with nitrogen. Heat slowly to 110° C. and continue heating under vacuum. Take samples for weight loss test. Continue heating under vacuum until weight loss on samples taken indicates no more than 0.5 per cent loss, then cool to obtain stripped base.

Example 5

Preparation of Aliquots (Parts A and B) Ready for Cross-Linking

Screen strip base through 325 mesh steel wire screen under pressure. Divide the batch into two equal parts, Part A and Part B. Mix into Part A the organoplatinum catalyst to provide 8 parts per million by weight. Take small samples from Part B and mix in the crosslinker (liquid organohydrogen polysiloxane having the formula $R_2HSiO_{1/2}$ with the R groups being predominantly methyl). Control the crosslinker level, so as to obtain a Shore durometer hardness of approximately 35 (ASTM D2240) in the crosslinked product. Thereafter, gradually add increasing amounts of the inhibitor (1,2,3,4 tetramethyl-1,2,3,4-tetravinyl cyclotetrasiloxane) to Part B and test mixed samples of Parts A and B to obtain a working time of about 6 hours at room temperature. Depending on the above-noted sample test results, the crosslinker is added to Part B to provide 1–6 pph by weight, and the inhibitor is added to Part B to provide 0.01 to 0.2 pph by weight.

Optionally, intimately mix in the UV light absorber 2-(2'-hydroxy-3'-t-butyl-5'-vinyl-phenyl)-5-chloro-2H-benzotriazole in an amount corresponding to approximately 0.5 wt % in Part B.

Screen Part A and Part B separately from one another on 325 mesh screen to remove any solid contaminants. For crosslinking or curing to obtain intraocular lenses, proceed in accordance with procedures required for liquid injection molding, or cast molding.

While this invention has been described with respect to various specific examples and embodiments, it is to be understood that the invention is not limited thereto and that it can be variously practiced within the scope of the following claims.

What is claimed is:

1. An intraocular lens for surgical implantation into a mammalian eye having a deformable lens body including an optically clear material comprising:
   a silicone polymer; and
   a silica reinforcer present in an amount effective to reinforce said polymer, the silica reinforcer including at least one aryl group effective to increase the refractive index of the silica reinforcer relative to a similar silica reinforcer without at least one aryl group, wherein the silica reinforcer has a refractive index greater than about 1.50.

2. The intraocular lens of claim 1 wherein the silicone polymer includes aryl groups.

3. The intraocular lens of claim 1 wherein the silicone polymer is a crosslinked polysiloxane.

4. The intraocular lens of claim 1 wherein the silicone polymer is a crosslinked copolymer of (1) at least one polysiloxane including aryl groups and (2) at least one crosslinker component.

5. The intraocular lens of claim 2 wherein said aryl groups are selected from the class consisting of phenyl, substituted phenyl groups, styryl, substituted styryl groups and mixtures thereof.

6. The intraocular lens of claim 1 wherein the silica reinforcer includes covalently bonded silicone-containing moieties including at least one aryl group.

7. The intraocular lens of claim 4 wherein the at least one polysiloxane has the formula:

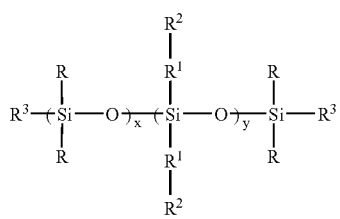

wherein each R is independently selected from the group consisting of alkyl radicals, substituted alkyl radicals, cycloalkyl radicals, substituted cycloalkyl radicals, aryl radicals and substituted aryl radicals, each $R^1$ is inddpendently selected from the group consisting of divalent hydrocarbon radicals and substituted divalent hydrocarbon radicals, each $R^2$ is independently selected from the group consisting of aryl radicals and substituted aryl radicals, each R is independently selected from the group consisting of monovalent hydrocarbon radicals having a carbon-carbon multiple bond and substituted hydrocarbon radicals having a carbon-carbon multiple bond, x is an integer in a range of 0 to about 500, and y is an integer in a range of about 6 to about 500.

8. A composition comprising:
   a silicone polymer; and
   a silicone reinforcer present in an amount effective to reinforce said polymer, the silica reinforcer including at least one aryl group effective to increase the refractive index of the silica reinforcer relative to a similar silica reinforcer without at least one aryl group,
   wherein the silicone polymer includes at least one polysiloxane of the formula:

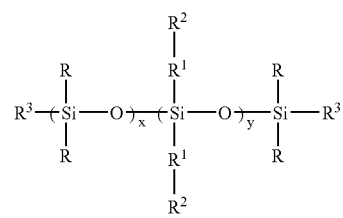

wherein each R is independently selected from the group consisting of alkyl radicals, substituted alkyl radicals, cycloalkyl radicals, substituted cycloalkyl radicals, aryl radicals and substituted aryl radicals, each $R^1$ is independently selected from the group consisting of divalent hydrocarbon radicals and substituted divalent hydrocarbon radicals, each $R^2$ is independently selected from the group consisting of aryl radicals and substituted aryl radicals, each $R^3$ is independently selected from the group consisting of monovalent hydrocarbon radicals having a carbon-carbon multiple bond and substituted hydrocarbon radicals having a carbon-carbon multiple bond, x is an integer in a range of 0 to about 500, and y is an integer in a range of about 6 to about 500.

9. The composition of claim 8 wherein the silicon polymer includes aryl groups.

10. The composition of claim 8 wherein the silicone polymer is a crosslinked polysiloxane.

11. The composition of claim 8 wherein the silica reinforcer has a refractive index of about 1.46 or higher.

12. The composition of claim 8 wherein the silicone polymer is a crosslinked copolymer of (1) at least one polysiloxane including aryl groups and (2) at least one crosslinker component.

13. The composition of claim 8 wherein said aryl groups are selected from the class consisting of phenyl, substituted phenyl groups, styryl, substituted styryl groups and mixtures thereof.

14. The composition of claim 8 wherein the silica reinforcer includes covalently bonded silicon-containing moieties including at least one aryl group.

15. The composition of claim 14 wherein the moeities include 1 to 3 aryl groups per silicone atom.

16. A polysiloxane compound having the following formula:

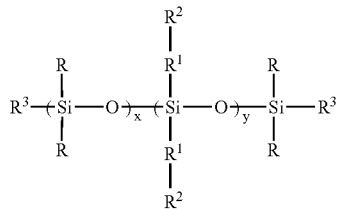

wherein each R is independently selected from the group consisting of alkyl radicals, substituted alkyl radicals, cycloalkyl radicals, substituted cycloalkyl radicals, aryl radicals and substituted aryl radicals, each $R^1$ is independently selected from the group consisting of divalent hydrocarbon radicals and substituted divalent hydrocarbon radicals, each $R^2$ is independently selected from the group consisting of aryl radicals and substituted aryl radicals, each $R^3$ is independently selected from the group consisting of monovalent hydrocarbon radicals having a carbon-carbon multiple bond and substituted hydrocarbon radicals having a carbon-carbon multiple bond, x is an integer in a range of 0 to about 500, and y is an integer in a range of about 6 to about 500.

17. The compound of claim 16, wherein each —$R^1$—$R^2$ is independently selected from the group consisting of styryl and substituted styryl radicals.

18. The compound of claim 16, wherein x/y is less than about 4.

19. The compound of claim 16, wherein each R is methyl.

20. The compound of claim 16, wherein each $R^1$ is independently selected from the group consisting of ethylene radical and methylene radical.

21. The compound of claim 16, wherein each $R^2$ is phenyl.

22. The compound of claim 16, wherein each $R^3$ is vinyl.

23. The intraocular lens of claim 1, wherein the silica reinforcer has a refractive index greater than or equal to about 1.47.

24. An intraocular lens for surgical implantation into a mammalian eye having a deformable lens body including an optically clear material comprising:
a silicone polymer; and
a silica reinforcer present in an amount effective to reinforce said polymer, the silica reinforcer including at least one aryl group effective to increase the refractive index of the silica reinforcer relative to a similar silica reinforcer without at least one aryl group, wherein the silica reinforcer has a refractive index greater than about 1.47; and
wherein the silicone polymer has a refractive index, and wherein the refractive index of the silica reinforcer is within about 0.015 of the refractive index of the silicone polymer.

25. The intraocular lens of claim 24 wherein the silicone polymer includes aryl groups.

26. The intraocular lens of claim 24 wherein the silicone polymer is a crosslinked polysiloxane.

27. The intraocular lens of claim 24 wherein the silicone polymer is a crosslinked copolymer of (1) at least one polysiloxane including aryl groups and (2) at least one crosslinker component.

28. The intraocular lens of claim 25 wherein said aryl groups are selected from the class consisting of phenyl, substituted phenyl groups, styryl, substituted styryl groups and mixtures thereof.

29. The intraocular lens of claim 24 wherein the silica reinforcer includes covalently bonded silicone-containing moieties including at least one aryl group.

30. The intraocular lens of claim 27 wherein the at least one polysiloxane has the formula:

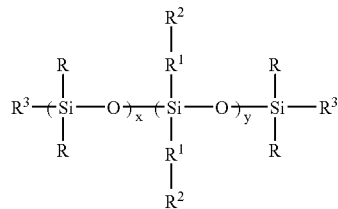

wherein each R is independently selected from the group consisting of alkyl radicals, substituted alkyl radicals, cycloalkyl radicals, substituted cycloalkyl radicals, aryl radicals and substituted aryl radicals, each $R^1$ is independently selected from the group consisting of divalent hydrocarbon radicals and substituted divalent hydrocarbon radicals, each $R^2$ is independently selected from the group consisting of aryl radicals and substituted aryl radicals, each $R^3$ is independently selected from the group consisting of monovalent hydrocarbon radicals having a carbon-carbon multiple bond and substituted hydrocarbon radicals having a carbon-carbon multiple bond, x is an integer in a range of 0 to about 500, and y is an integer in a range of about 6 to about 500.

* * * * *

UNITED STATES PATENT AND TRADEMARK OFFICE
CERTIFICATE OF CORRECTION

PATENT NO. : 7,066,955 B2
APPLICATION NO. : 10/676579
DATED : June 27, 2006
INVENTOR(S) : Michael D. Lowery Page 1 of 1

It is certified that error appears in the above-identified patent and that said Letters Patent is hereby corrected as shown below:

Column 13, Claim 7, Line 64: "each $R^1$ is inddpen-" should read --each $R^1$ is indepen- --

Column 14, Claim 7, Line 2: "R is independently" should read --$R^3$ is independently--

Column 15, Claim 23: Claim 23 which was claim 28 in the application was canceled by the Examiner under Examiner's Amendment in the Notice of Allowance.

Column 15, Claim 24: Should now be renumbered to Claim 23.

Column 16, Claim 25: Should now be renumbered to Claim 24. "lens of claim 24 wherein the" should now read --lens of claim 23 wherein the--

Column 16, Claim 26: Should now be renumbered to Claim 25. "lens of claim 24 wherein the" should now read --lens of claim 23 wherein the--

Column 16, Claim 27: Should now be renumbered to Claim 26. "lens of claim 24 wherein the" should now read --lens of claim 23 wherein the--

Column 16, Claim 28: Should now be renumbered to Claim 27. "lens of claim 25 wherein said" should now read --lens of claim 24 wherein said--

Column 16, Claim 29: Should now be renumbered to Claim 28. "lens of claim 24 wherein the" should now read --lens of claim 23 wherein the--

Column 16, Claim 30: Should now be renumbered to Claim 29. "lens of claim 27 wherein the" should now read --lens of claim 26 wherein the--

Signed and Sealed this

Sixteenth Day of January, 2007

JON W. DUDAS
*Director of the United States Patent and Trademark Office*